(12) United States Patent
Schuschnig et al.

(10) Patent No.: US 11,666,712 B2
(45) Date of Patent: Jun. 6, 2023

(54) NEBULIZER AND METHOD FOR PRODUCING A NEBULIZER

(71) Applicant: PARI GmbH Spezialisten für effektive Inhalation, Starnberg (DE)

(72) Inventors: Uwe Schuschnig, Munich (DE); Ulf Krüger, Munich (DE); Titus Selzer, Munich (DE); Erman Lu, Icking (DE); Emir Jelovac, Munich (DE); Jens Gramann, Gräfelfing (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 0 days.

(21) Appl. No.: 15/328,989

(22) PCT Filed: May 12, 2015

(86) PCT No.: PCT/EP2015/060454
§ 371 (c)(1),
(2) Date: Jan. 25, 2017

(87) PCT Pub. No.: WO2016/015889
PCT Pub. Date: Feb. 4, 2016

(65) Prior Publication Data
US 2017/0224937 A1     Aug. 10, 2017

(30) Foreign Application Priority Data
Jul. 31, 2014   (DE) .................... 10 2014 215 064.7

(51) Int. Cl.
*A61M 11/06*     (2006.01)
*A61M 11/00*     (2006.01)
*A61M 15/00*     (2006.01)

(52) U.S. Cl.
CPC .......... *A61M 11/06* (2013.01); *A61M 11/002* (2014.02); *A61M 11/003* (2014.02);
(Continued)

(58) Field of Classification Search
CPC .. A61M 11/06; A61M 11/002; A61M 11/003; A61M 15/00; A61M 2205/75
See application file for complete search history.

(56) References Cited

U.S. PATENT DOCUMENTS 3,425,414 A   2/1969 Roche
4,995,385 A   2/1991 Valentini et al.
(Continued)

FOREIGN PATENT DOCUMENTS

CN   1330563 A   1/2002
CN   1516606 A   7/2004
(Continued)

OTHER PUBLICATIONS

International Search Report and Written Opinion dated Jul. 8, 2015 in connection with International Application No. PCT/EP2015/060454.
(Continued)

*Primary Examiner* — Christopher R Dandridge
(74) *Attorney, Agent, or Firm* — Wolf, Greenfield & Sacks, P.C.

(57) ABSTRACT

The invention relates to a nebulizer (1) comprising an aerosol generator (6), a nebulizing chamber (5) and an outlet (16), the aerosol generator (6) being designed to release an aerosol into the nebulizing chamber (5) and the outlet (16) being designed to allow the removal of the aerosol from the nebulizing chamber (5). To achieve a high output rate, a wetting surface (2) is provided in the nebulizing chamber (5).

17 Claims, 5 Drawing Sheets

(52) U.S. Cl.
CPC ......... *A61M 15/00* (2013.01); *A61M 2205/75* (2013.01); *A61M 2206/14* (2013.01); *A61M 2207/00* (2013.01)

(56) References Cited

U.S. PATENT DOCUMENTS

| | | | |
|---|---|---|---|
| 5,950,619 | A | 9/1999 | van der Linden et al. |
| 5,957,389 | A * | 9/1999 | Wunderlich ........... A61M 11/06 |
| | | | 239/338 |
| 5,970,974 | A | 10/1999 | van der Linden et al. |
| 6,432,084 | B1 * | 8/2002 | Levinson ................ A61M 11/02 |
| | | | 604/118 |
| 6,543,443 | B1 | 4/2003 | Klimowicz et al. |
| 6,880,555 | B1 | 4/2005 | Brunnberg et al. |
| 6,994,083 | B2 * | 2/2006 | Foley .................... A61M 11/06 |
| | | | 128/200.14 |
| 7,611,072 | B2 * | 11/2009 | Peters ................. A61M 11/041 |
| | | | 239/13 |
| 7,735,485 | B2 | 6/2010 | Yamashita et al. |
| 7,954,486 | B2 | 6/2011 | Papania et al. |
| 8,006,698 | B2 * | 8/2011 | Boehm ................. A61M 15/08 |
| | | | 128/207.18 |
| 8,596,264 | B2 * | 12/2013 | Sommer ................ A61M 11/06 |
| | | | 128/200.21 |
| 8,656,908 | B2 | 2/2014 | Papania et al. |
| 10,376,661 | B2 | 8/2019 | Gallem et al. |
| 2002/0129812 | A1 | 9/2002 | Litherland et al. |
| 2003/0049396 | A1 | 3/2003 | Oles et al. |
| 2004/0031485 | A1 | 2/2004 | Rustad et al. |
| 2005/0161041 | A1 | 7/2005 | Schuler et al. |
| 2006/0207591 | A1 | 9/2006 | Gallem et al. |
| 2006/0289002 | A1 | 12/2006 | Hetzer et al. |
| 2007/0031639 | A1 * | 2/2007 | Hsu .......................... B05D 5/08 |
| | | | 428/141 |
| 2007/0076067 | A1 | 4/2007 | Hamano et al. |
| 2007/0151562 | A1 | 7/2007 | Jones et al. |
| 2007/0154407 | A1 | 7/2007 | Peters et al. |
| 2008/0060640 | A1 | 3/2008 | Waldner et al. |
| 2008/0283049 | A1 | 11/2008 | Mahoney et al. |
| 2008/0299049 | A1 | 12/2008 | Stangl |
| 2009/0013994 | A1 | 1/2009 | Jones et al. |
| 2009/0137950 | A1 | 5/2009 | Loenner et al. |
| 2009/0223515 | A1 | 9/2009 | Watanabe |
| 2009/0283611 | A1 * | 11/2009 | Varanasi ................. B05B 7/066 |
| | | | 239/366 |
| 2009/0293868 | A1 | 12/2009 | Hetzer et al. |
| 2010/0006113 | A1 | 1/2010 | Urtsev et al. |
| 2010/0083963 | A1 | 4/2010 | Wharton et al. |
| 2011/0114090 | A1 | 5/2011 | Piper |
| 2012/0103330 | A1 * | 5/2012 | David .................... C23C 16/325 |
| | | | 128/203.12 |
| 2013/0239956 | A1 | 9/2013 | Schulz et al. |
| 2015/0238712 | A1 | 8/2015 | Gallem et al. |
| 2017/0143915 | A1 * | 5/2017 | Strange ................ A61M 11/007 |

FOREIGN PATENT DOCUMENTS

| | | |
|---|---|---|
| CN | 1960777 A | 5/2007 |
| CN | 101547717 A | 9/2009 |
| CN | 101579666 A | 11/2009 |
| DE | 19602628 A1 | 7/1997 |
| DE | 200 06 010 U1 | 7/2000 |
| DE | 10 2005 057 685 A1 | 6/2007 |
| EP | 0 786 263 A2 | 7/1997 |
| EP | 1 040 874 A2 | 10/2000 |
| EP | 1 142 600 A1 | 10/2001 |
| EP | 2 062 608 A2 | 5/2009 |
| JP | S53-059818 A2 | 5/1978 |
| JP | S54-160873 U | 11/1979 |
| JP | H03-126734 A | 5/1991 |
| JP | H05-200329 A | 8/1993 |
| JP | H05200329 * | 8/1993 |
| JP | H10-237 A | 1/1998 |
| JP | 2000-336194 A | 12/2000 |
| JP | 2013-48935 A | 3/2013 |
| WO | WO 99/04840 A1 | 2/1999 |
| WO | WO 99/42154 A1 | 8/1999 |
| WO | WO 01/26720 A1 | 4/2001 |
| WO | WO 01/56639 A1 | 8/2001 |
| WO | WO 01/74672 A1 | 10/2001 |
| WO | WO 01/87393 A2 | 11/2001 |
| WO | WO 03/061745 A1 | 7/2003 |
| WO | WO 05/030305 A1 | 4/2005 |
| WO | WO 2006/006963 A2 | 1/2006 |
| WO | WO 2011/0546931 A1 | 5/2011 |
| WO | WO 2013/030117 A2 | 3/2013 |
| WO | WO2013030117 * | 3/2013 ........... A61M 11/06 |

OTHER PUBLICATIONS

International Preliminary Report on Patentability dated Feb. 9, 2017 in connection with International Application No. PCT/EP2015/060454.

International Search Report and Written Opinion for corresponding International Application No. PCT/EP2013/068592 dated Nov. 7, 2013.

International Preliminary Report on Patentability for corresponding International Application No. PCT/EP2013/068592 dated Mar. 17, 2015.

Extended Search Report from corresponding European Application No. 12184036.7 dated Dec. 6, 2012.

English translation of Chinese Examination Report from corresponding Chinese Application No. 201380047513.1 dated Oct. 5, 2016.

Chinese Search Report dated Jan. 3, 2018 in connection with Chinese Application No. 201380047513.1 and English translation thereof.

Japanese Notice of Grounds of Rejection dated Nov. 20, 2018 in connection with Japanese Application No. 2017-505162.

Kharitonov et al., Surface modification of polymers by direct fluorination: A convenient approach to improve commercial properties of polymeric articles. Pure Appl. Chem. 2009; 81(3):451-471.

Lee et al., The Wettability of Fluoropolymer Surfaces: Influence of Surface Dipoles. Langmuir. 2008; 24:4817-4826.

Du Toit et al., The effect of surface fluorination on the wettability of high density polyethylene. Journal of fluorine chemistry. Sep. 1, 1995;74(1):43-8.

Chinese 3rd Office Action and Search Report for Chinese Application No. CN 201580050170.3 dated Mar. 3, 2021, together with an English language translation.

Chinese Office Action dated Nov. 24, 2021 in connection with Chinese Application No. 201580050170.3, and English translation thereof.

* cited by examiner

NEBULIZER AND METHOD FOR PRODUCING A NEBULIZER

CROSS REFERENCE TO RELATED APPLICATIONS

This application is a National Stage application of PCT/EP2015/060454, filed May 12, 2015, which claims priority to German Patent Application No. 10 2014 215 064.7, filed Jul. 31, 2014, which are hereby incorporated by reference in their entirety.

The invention relates to a nebulizer comprising an aerosol generator as well as to a method for producing a nebulizer.

Known from DE 19602628 A1 are nebulizers comprising a nozzle arranged in a nebulizing chamber and an air inlet pipe protruding into the nebulizing chamber.

The object of the invention is to provide a nebulizer with which a high output rate can be achieved as well as a method for producing such a nebulizer. This object is solved by a nebulizer having the features of claim 1 and by a method having the features of claim 11.

According to one embodiment, the object is also solved by a nebulizer comprising an aerosol generator, a nebulizing chamber and an outlet, wherein the aerosol generator is configured to release an aerosol into the nebulizing chamber, the outlet is configured to allow removal of the aerosol from the nebulizing chamber, and a wetting surface is provided in the nebulizing chamber, the wetting surface being provided on a plastic component.

Output rate is to be understood as the amount of aerosol that passes through the outlet over time.

An aerosol is a mixture of particles suspended in a gas. The suspended particles can be solid or liquid. Both solid and liquid suspended particles may also be present. Aerosol droplets are liquid droplets in a gas.

A nebulizer is a device that is configured to provide and release an aerosol.

An aerosol generator is a device that is configured to generate an aerosol. An aerosol generator is preferably a device that is configured to generate liquid droplets and to mix these with a gas. An aerosol generator preferably comprises a nebulizer, an atomizer, a humidifier, a compressed air nebulizer, an air atomizer, an electronic nebulizer, an ultrasonic nebulizer, an electrohydrodynamic nebulizer, an electrostatic nebulizer, a membrane nebulizer, a nebulizer having a vibrating membrane, an electronic nebulizer having a vibrating membrane, a mesh nebulizer, a nozzle nebulizer, an inhaler (MDI), a powder atomizer (DPI) or a combination thereof. In one embodiment, the inhaler comprises a pressurized canister comprising a medicament and a propellant. The canister is expediently connected to an actuator that can be operated by hand. It is advantageous for the inhaler to be configured so as to release a specific amount of medicament in aerosol form upon activation. In one embodiment, the aerosol generating device is configured for use with ventilators.

A nebulizing chamber is a space that is configured such that aerosol can flow therethrough. A nebulizing chamber can be a space that is configured to accommodate, at least temporarily, an aerosol.

An outlet is a device that is provided to allow an aerosol out of the nebulizing chamber. The outlet is expediently configured to be connected to a component such as a mouthpiece or a mask.

A plastic component is a component comprising a plastic. The component can be made entirely of plastic. The plastic can be an organic, polymeric solid, which has been produced synthetically or semi-synthetically from monomeric organic molecules or biopolymers. The plastic can be a thermoplastic, a thermoset or an elastomer. The plastic component can comprise, for example, a polypropylene.

A wetting surface is a surface that is configured to be wetted by a liquid. Wetting takes place when a liquid forms a contact angle of 90 degrees or less with the wetting surface.

In one embodiment, the wetting surface has, at least temporarily, preferably permanently, a surface tension of 32 to 5000 millinewtons per meter (mN/m). The surface tension is preferably between 35 and 400 millinewtons per meter (mN/m), particularly preferred between 44 and 73 millinewtons per meter (mN/m). The surface tension can be between 50 and 72 millinewtons per meter (mN/m).

The wetting surface can comprise a wetting material. Preferred wetting materials are metals and glass. In one embodiment, the wetting surface comprises ABS.

The wetting surface can have a predetermined surface roughness. The average roughness value $R_a$ can be between 6.3 and 0.006. The average roughness value $R_a$ is preferably between 1.6 and 0.01, particularly preferred between 0.5 and 0.006. The surface roughness is preferably provided by a correspondingly configured mold, such as an injection mold or a die casting mold, and a corresponding production process.

The wetting surface can be cleaned.

The wetting surface can have a temperature of between 20 and 80 degrees, preferably between 40 and 50 degrees.

The wetting surface can have a surface treatment.

The wetting surface is preferably printed or coated, and it is particularly preferred for it to be lacquered or laminated.

The wetting surface can be blasted. It can be blasted in particular with sand, glass beads, ceramics, steel, dry ice, corundum, steel grit, steel balls, cut wire, emery, bronze grit, blast furnace slag, calcium carbonate granules or plastics.

The wetting surface can be corona treated, flame treated, fluorinated, plasma treated, in particular oxygen plasma treated or low-pressure plasma treated, ozone treated or UV light treated. It is particularly preferred for the wetting surface to be a fluorinated wetting surface. The fluorinated wetting surface has preferably been obtained by replacing hydrogen atoms of a polymer chain with fluorine atoms. The fluorinated surface or fluorinated wetting surface has been exposed to fluorine, expediently a fluorine mixture. This preferably occurred at room temperature, particularly preferred at 25° C. It is expedient if no temperature peaks thereby occurred. The depth of penetration of the fluorine atoms into the substrate is preferably in the molecular range. The properties of the base material have preferably remained unchanged. The base material comprises plastic, and the base material preferably comprises ABS, EPDM, plastic from renewable resources, NBR, HNBR, PEEK, PMMA, polyamide, polyester, polyethylene, LDPE, UHMW-PE, POM, PET, EPDM, PBT, polycarbonate, polyphenyl sulfide, polysiloxane elastomer, polymer containing glass fiber, copolymers, polypropylene, silicone, rubber or TPE. The surface energy of the wetting surface can have been adapted to the surface energy of a liquid. The liquid preferably comprises saline solution or a medicament.

In one embodiment, the fluorinated wetting surface has been obtained by gas phase fluorination. During gas phase fluorination, the object or component is exposed to fluorine, expediently a fluorine mixture in gas form such that hydrogen atoms are replaced by fluorine atoms in the outermost surface layer. A surface of a component can thereby be treated relatively independently of its geometry. The fluorinated wetting surface has preferably been achieved by treating the component in a vacuum reactor. The fluorinated component can have been treated as bulk material in a preferably cylindrical chamber. It is advantageous for the fluorinated component to have been inserted into a preferably cubic chamber in a basket, a mesh box or a specific load carrier. The fluorinated component can have been treated in a continuous flow reactor.

In one embodiment, the fluorinated wetting surface has been obtained by further processing fluorinated powder or granulate by means of injection molding or blow molding. The powder or granulate can thereby have been fluorinated in such a manner that the fluorine atoms are located solely in an outer area of the powder particles or granules. The fluorine atoms can also have penetrated deeper into the powder particles or granules or can be located in all areas of the powder particles or granules. The powder or granulate has been expediently fluorinated using gas phase fluorination. Polyolefin powder or granulate has preferably been used for this purpose. The fluorination of the powder or granulate has preferably occurred in a rotating drum having scoop components or in a reactor having a movable stirrer. It is expedient for the reactor to be cylindrical and for the stirrer to be configured such that it rotates.

A surface with a highly polar nature that is active over a long period of time can thereby have been achieved without influencing the base material. The fluorination of the surface is preferably not reversible. A barrier layer, preferably a permeation layer, can have been formed. Permeation, diffusion, migration, friction, adhesion and adhesiveness can have been reduced. Adherence, film formation, adhesion and wettability can have been increased. An improved drainage of liquids, quicker drying, a higher print quality, improved cleanliness owing to the fact there is no adherence of dirt particles, as well as reduced calcification and mold formation, improved assemblability or an optically more attractive surface can have been achieved. Owing to the barrier layer, it can be prevented that components of plastic material diffuse out of the surface or that the filling of a container penetrates a wall. Unpleasant odors, environmental burdens, swelling, a greasy surface and the peeling off of labels can be prevented. The achieved property can have long-term stability even after cleaning and sterilization processes. A surface of a workpiece can be fluorinated such that the dimensions of the workpiece are the same before and after fluorination. An antibacterial or antimicrobial effect can have been achieved. The antibacterial or antimicrobial effect can be temporary.

The wetting surface can have been subjected to surface activation.

By providing the wetting surface, it can be achieved that liquid droplets that reach a surface of the nebulizing chamber gather on the wetting surface. A liquid film can be formed. It is also possible to achieve the effect that liquid slides off of the surface.

This is advantageous since, on surfaces that are not wettable or are only poorly wettable, liquid droplets can form which protrude a long way from the surface. As a result hereof, a flow-throughable cross-section of the nebulizing chamber can be reduced. A reduced cross-section can result in more aerosol droplets impinging upon and adhering to the surfaces of the nebulizing chamber and the liquid droplets already present on the surface. These aerosol droplets are then unable to arrive at the outlet.

Furthermore, large droplets can detach from a poorly wettable surface and can drop down through a space through which an aerosol is flowing. Aerosol droplets are entrained therewith, which are then no longer able to arrive at the outlet. As a result, the output rate is reduced.

In one embodiment, a wetting surface is provided such that a liquid film can form thereon and that droplets which collide with the liquid film can produce further droplets.

In one configuration, the respirable rate can be increased by up to 30%. For this purpose, a surface treatment is preferably provided on a nozzle attachment and a lower part of the nebulizer. In preferred configurations, the duration of therapy can be reduced by 20%, the residual volume can be reduced, the patient can receive a higher dose of medicament in a shorter time and the efficiency of the nebulizer can be increased. These properties preferably remain even after cleaning in a dishwasher and after 10 autoclave cycles at 134° C.

In one embodiment, the aerosol generator comprises a nozzle. In the combination with a nozzle it is particularly expedient to provide a wetting surface since nozzles can generate aerosols with particles that have large differences in diameter. As a result, it is rather very large liquid droplets which adhere to surfaces of a nebulizing chamber. These can greatly reduce a cross-section though which a flow is to pass and can greatly reduce the output rate.

The nozzle is preferably provided with a liquid supply and configured such that gas can flow therethrough. The nozzle can be configured as a two-substance nozzle with internal mixing or as a two-substance nozzle with external mixing.

It is expedient for the nebulizing chamber to comprise an aerosol guide that connects the aerosol generator to the outlet, and for the aerosol guide to comprise the wetting surface. A large part of the aerosol that is suitable for being guided to the outlet can thus arrive at the outlet.

The aerosol guide is preferably a hollow space, through which the generated aerosol must pass to arrive at the outlet. The aerosol guide expediently comprises a continuous path, along which the aerosol can pass through the aerosol guide.

The aerosol guide can be partially provided with the wetting surface and is preferably entirely coated with the wetting surface.

In one embodiment, a surface of the aerosol guide comprises the wetting surface. Since surfaces are easy to process, a cross-section of the aerosol guide can thus be at least largely maintained in a simple manner.

A surface is preferably a two-dimensional boundary surface of a body. A surface can be flat, a surface can also be curved.

If an edge of the aerosol guide has the wetting surface, it can be achieved that liquid gathers particularly well at the edge. The wetting surface is preferably configured such that liquid flows away well from the edge. The effect that liquid accumulates at the edge in such a manner that the edge is shifted can be reduced or prevented.

This is particularly desirable in the case of edges that have a function. The function may be to provide a defined cross-section, such as in the case of an aperture. A function may also be to provide a defined path for filtering out undesirable components in the aerosol. The edge can thereby delimit a filter area, as described below, which is provided to filter out aerosol droplets having a predetermined diameter from an aerosol flow.

In one embodiment, the aerosol guide comprises a passage and the passage has the wetting surface. As a result hereof, it can be achieved that the cross-section of the aerosol guide is largely or completely maintained at a position that is particularly important for the output rate.

A passage is preferably an area in the aerosol guide that has a smaller cross-section than adjacent areas. A passage can be a narrowing, which is configured to influence pressures or speeds of fluids flowing therethrough, such as a nozzle or an aperture.

It is advantageous for the nebulizing chamber to have a delimiting wall comprising the wetting surface. It can hereby be achieved that comparatively large amounts of liquid are quickly guided back into a reservoir. Furthermore, the residual amount that remains in the nebulizer after use and is not made available to the patient can be reduced particularly well in such a manner.

A delimiting wall is a wall which delimits the nebulizing chamber from its surroundings.

The nebulizing chamber can comprise an air supply which has the wetting surface. The supplied air can thus be guided in a particularly precise manner.

An air supply is configured such that it can allow ambient air into the nebulizing chamber. In one embodiment, the air supply is configured to conduct ambient air past the aerosol generator to the outlet. The aerosol can thereby be effectively guided to the outlet.

The air supply is preferably configured as an air inlet pipe.

In one embodiment, the nebulizing chamber comprises a baffle surface and the baffle surface comprises the wetting surface. It can be achieved in this manner that aerosol droplets applied to the baffle surface influence the surface and contour of the baffle surface to the smallest possible extent. A constant function of the baffle surface can be achieved.

A baffle surface is a surface that is configured such that aerosol moves against it. Upon contacting the baffle surface, aerosol droplets can break up into smaller aerosol droplets.

A baffle surface can be provided on an airflow control. The airflow control can be provided at the outlet of a fluid stream. In one embodiment, the airflow control is arranged in the fluid stream opposite a discharge opening. The discharge opening is expediently the discharge opening of a nozzle, preferably a gas nozzle.

A baffle surface can be provided on a baffle. A baffle is a component that is arranged adjacent to an aerosol generator.

The baffle is preferably arranged such that aerosol droplets having a diameter which is larger than a predetermined diameter can collide therewith. For this purpose, it extends in one embodiment at least in a plane around the aerosol generator. It can be configured in particular in a cylindrical, frustoconical or conical manner.

The provision of a wetting surface on a baffle can be particularly advantageous if the aerosol guide is designed such that a particularly small flow-throughable cross-section is provided on the baffle. Adhering liquid could reduce this cross-section even further such that less aerosol can flow to the outlet. By providing a wetting surface on the baffle, it can be achieved that the liquid arriving at the baffle can gather on the baffle to a greater extent and remove itself more quickly from the baffle.

In one embodiment, the nebulizing chamber comprises a filter area and the filter area comprises the wetting surface.

So that it is able to fulfill the function of a filter, a filter area can be arranged such that predominantly larger liquid droplets collide therewith and smaller liquid droplets are guided past it. This can be achieved by arranging the filter area in a region that is designed such that an aerosol experiences a change in direction. In such regions, larger and smaller liquid droplets typically predominantly distribute themselves in certain sub-regions such that it can be determined via the arrangement and configuration of the baffle surface which liquid droplets are filtered out.

The edge of the filter area can thereby determine which aerosol droplets are still filtered out and which aerosol droplets can pass through the filter area.

Owing to this function of the filter area, it is supplied with a particularly large amount of liquid droplets. However, this function also requires a precise shape of the filter area. The shape of the filter area can be changed in such a manner by liquid droplets disposed thereon that the droplet spectrum of the filtered-out liquid droplets is altered.

The droplet spectrum characterizes the occurrence of liquid droplets with certain diameters in the aerosol.

So as to keep the change to the shape of the filter area as minor as possible, it is expedient to provide the filter area with a wetting surface. As a result thereof, liquid droplets applied to the filter area can gather on the filter area in such a manner that they barely change the shape of the filter area. Furthermore, the wetting surface can be configured such that liquid droplets flow off thereof so well that they are removed quickly from the filter area and little liquid is disposed on the filter area.

A filter area can be provided on a nebulizing chamber divider. A nebulizing chamber divider is preferably configured to divide the nebulizing chamber such that the aerosol has to undergo a change in direction in order to be able to arrive at the outlet. In conjunction with this function, the nebulizing chamber divider can, in accordance with the principle described above, separate aerosol having a desired droplet spectrum from aerosol having an undesired droplet spectrum.

The filter area can be provided on a labyrinth guide. A labyrinth guide is an aerosol guide which requires the aerosol to change direction at least once, preferably at least twice or three times, when it is flown through. In conjunction with this property, the labyrinth guide can, in accordance with the principle described above, separate aerosol having a desired droplet spectrum from aerosol having an undesired droplet spectrum.

The filter area can be provided on a baffle. The baffle is, as described above, preferably arranged such that a predetermined droplet spectrum is guided against it. For this purpose, it extends, as described above, in one embodiment at least in a plane around the aerosol generator. It can be configured in particular in a cylindrical, frustoconical or conical manner. In order to be able to arrive at the outlet, the aerosol must expediently change direction in the region of the baffle, preferably adjacent to a surface, in particular adjacent to an edge of the baffle.

The baffle is thereby expediently arranged such that, in accordance with the principle described above, it prevents aerosol droplets that are not supposed to arrive at the outlet from travelling along the path to the outlet. Such aerosol droplets can be guided to a surface of the baffle such that they can collide therewith and adhere thereto. In one embodiment, the nebulizer is configured such that inhaled air can flow internally through the baffle past the aerosol generator, thereby taking aerosol with it, and continues to flow around the edge of the baffle and along an outer side of the baffle in the opposite direction. Aerosol droplets that are too large to follow this path are thereby deposited on the inner side of the baffle. The positioning of the edge of the baffle determines which aerosol droplets are still deposited on the baffle and which aerosol droplets are still able to continue further in the direction of the outlet. It is therefore also important here for the droplet spectrum of the aerosol to be guided to the outlet that the outer dimensions of the edge are not modified by adhering liquid since the filtered-out droplet spectrum can then change. As a result, it is particularly expedient to provide a wetting surface on the edge of the baffle, on the inner side of the baffle or on the entire baffle.

It is expedient for the nebulizing chamber to comprise a reservoir, for the aerosol generator to be configured to cooperate with the reservoir and for the reservoir to comprise the wetting surface. Liquid can consequently collect particularly well in a region of the reservoir intended therefore.

A reservoir is a storage means which is provided for storing liquids, in particular for storing medicaments. The reservoir is expediently configured to release liquid to the aerosol generator. It is advantageous for the nebulizer to be configured such that liquid that has deposited on surfaces in the nebulizing chamber can reach the reservoir.

The object is furthermore solved by a method for producing a nebulizer having a wetting surface, which comprises the steps of: producing a nebulizer comprising an aerosol generator, a nebulizing chamber and an outlet, said aerosol generator being configured to release an aerosol into the nebulizing chamber and said outlet being configured to allow removal of the aerosol from the nebulizing chamber, and providing a wetting surface in the nebulizing chamber, said wetting surface being provided by fluorination.

The invention will be described in more detail in the following by means of embodiment examples and with reference to the enclosed drawings.

Figure 1:
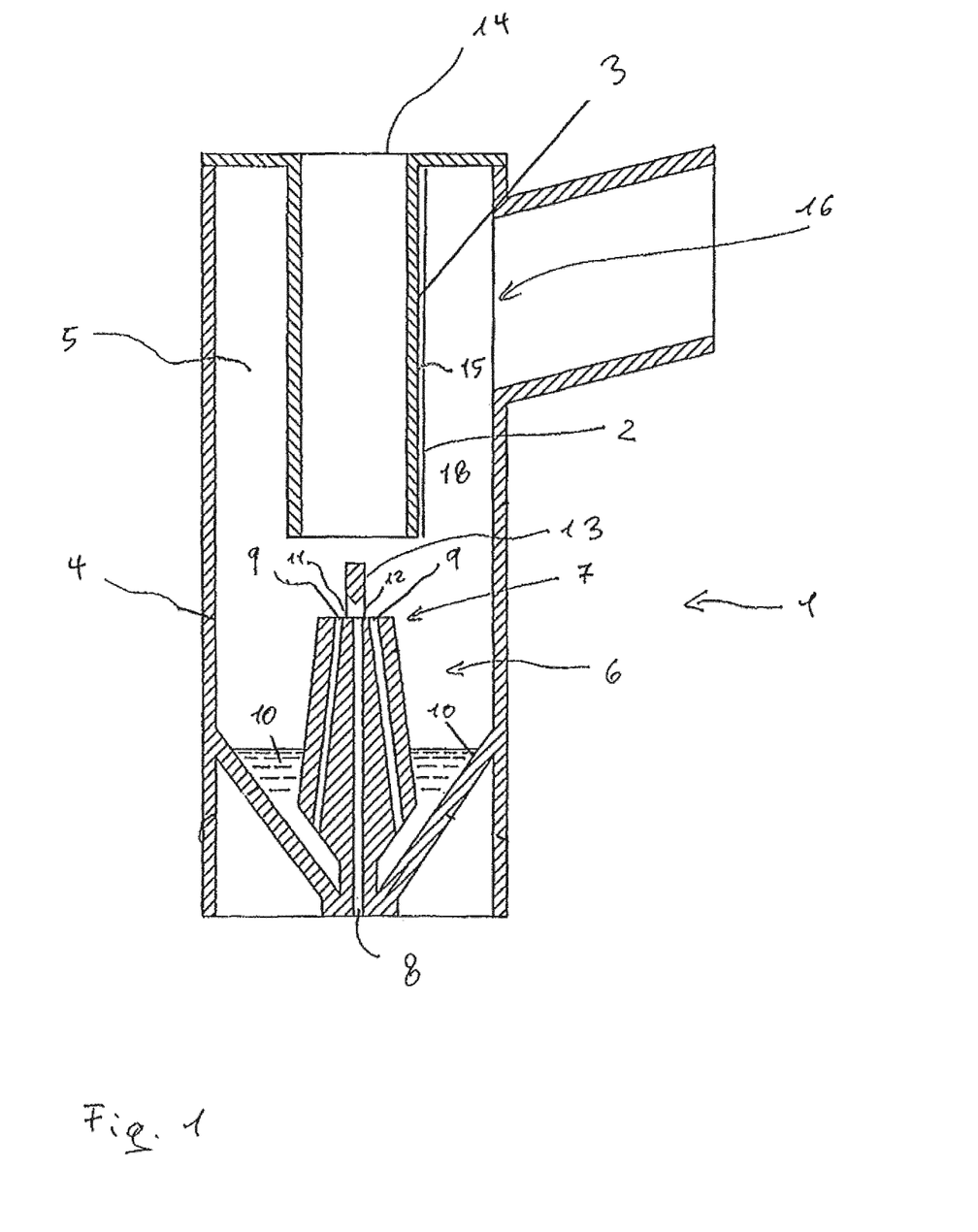
FIG. 1 shows an embodiment example of a nebulizer having a wetting surface on an air inlet pipe.

FIG. 1 shows an embodiment example of a nebulizer 1 having a wetting surface 2 on an air inlet pipe 3. The nebulizer 1 shown in FIG. 1 comprises a delimiting wall 4, which encloses a nebulizing chamber 5. Disposed in the nebulizing chamber 5 is an aerosol generator 6, which is configured as a two-substance nozzle 7. The two-substance nozzle 7 comprises one gas channel 8 and three liquid channels 9, although only two of the three liquid channels 9 are shown in FIG. 1. The gas channel 8 has a connection for a compressed air source which is not shown. The liquid channels 9 are configured to cooperate with a medicament reservoir 10. The gas channel 8 and the liquid channels 9 adjacently open out into an atomization region 11 of the two-substance nozzle 7. Provided opposite a mouth 12 of the gas channel 8 is an airflow control 13.

An air inlet pipe 3 extends from an inlet opening 14 of the delimiting wall 4 in the direction of the two-substance nozzle 7. The outer side 15 of the air inlet pipe 3 is provided with a wetting surface 2. The wetting surface 2 extends over the entire length and half of the circumference of the air inlet pipe 3. The wetting surface 2 thereby extends over that half of the circumference of the air inlet pipe 3 which is facing an outlet 16 provided in the delimiting wall 4.

During operation of the nebulizer 1, a liquid medicament from the medicament reservoir 10 reaches the atomization region 11 through the liquid channels 9. Compressed air also reaches the atomization region 11 through the gas channel 8. Upon inhaling, a patient sucks ambient air through the air inlet pipe 3 into the atomization region 11. An aerosol is produced in the atomization region 11 with the aid of the airflow control 13. Upon inhaling, the patient sucks aerosol out of the nebulizer 1 through the outlet 16. As a result hereof, medicament liquid lands on the inner side of the delimiting wall 4 and on the air inlet pipe 3. This medicament liquid reduces the size of the passage 18 between the delimiting wall 4 and the air inlet pipe 3. As a result, less aerosol can reach the patient.

This effect is lower on the wetting surface 2, as will be described in the following by means of FIGS. 2 and 3.

Figure 2:
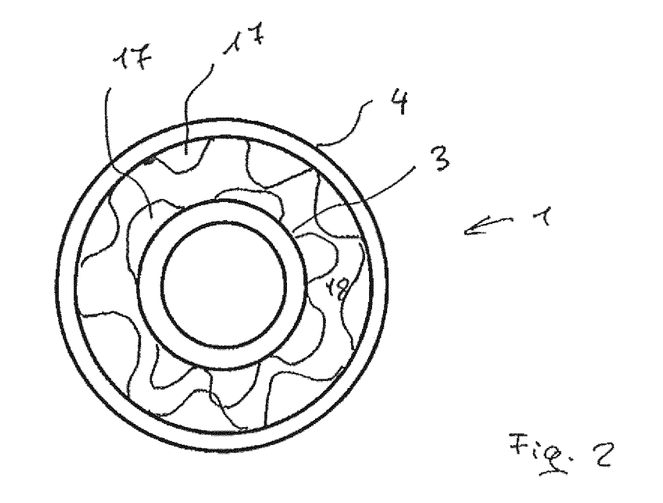
FIG. 2 shows a cross-section of a nebulizer without a wetting surface.

FIG. 2 shows a cross-section of a nebulizer 1 without a wetting surface. Fat liquid droplets 17 are disposed on the delimiting wall 4 and on the air inlet pipe 3. The passage 18 between the delimiting wall 4 and the air inlet pipe 3 is greatly reduced in size by the fat liquid droplets 17. Many of the aerosol droplets that are guided through this passage 18 from the atomization region 11 in the direction of the outlet 16 collide with the fat liquid droplets 17 and cannot arrive at the outlet 16.

Figure 3:
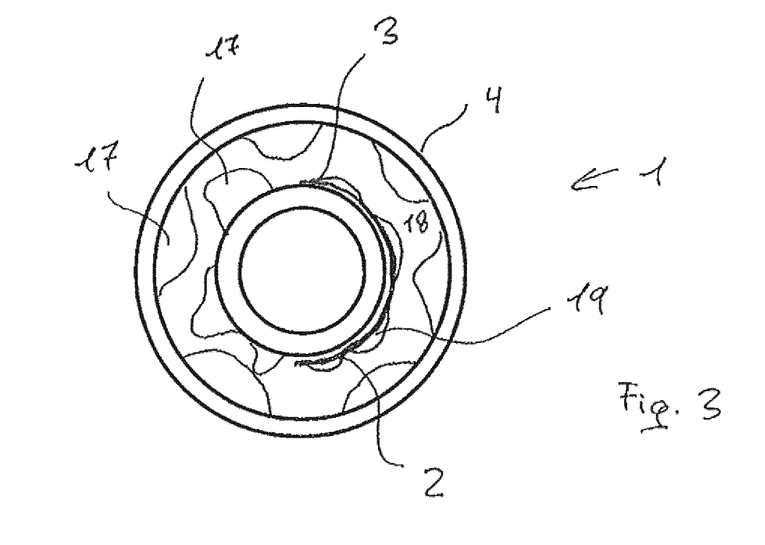
FIG. 3 shows a cross-section of the nebulizer shown in FIG. 1.

FIG. 3 shows a cross-section of the nebulizer 1 shown in FIG. 1. In this nebulizer 1, fat liquid droplets 17 are also disposed on the delimiting wall 4 and on the air inlet pipe 3. However, no fat liquid droplets 17 can be found in the region of the wetting surface 2, but rather flat liquid droplets 19. This is achieved owing to the good wettability of the wetting surface 2. Owing to the fact that there are no fat liquid droplets 17 on the wetting surface 2, the cross-section of the passage 18 is larger in this region. Fewer aerosol droplets collide with the flat liquid droplets 19. As a result, the output rate is greater than in a nebulizer 1 without a wetting surface 2.

Figure 4:
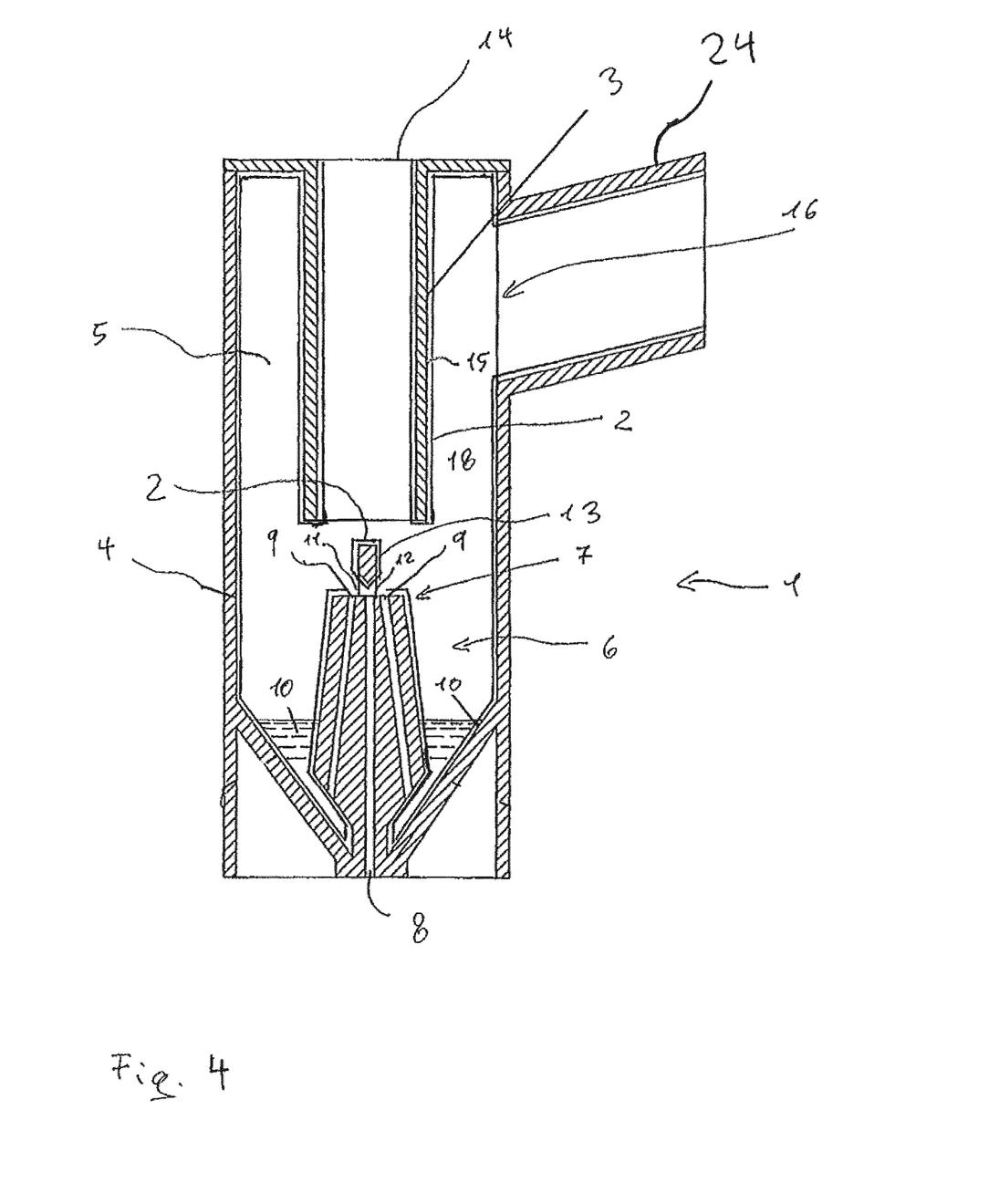
FIG. 4 shows a nebulizer, in which the entire nebulizing chamber is provided with the wetting surface.

FIG. 4 shows a nebulizer 1, in which the entire nebulizing chamber 5 has been provided with the wetting surface 2. The inner wall of the delimiting wall 4, the air inlet pipe 3, the inside of a connection 24, the two-substance nozzle 7 and the airflow control 13 are provided with the wetting surface 2.

Figure 5:
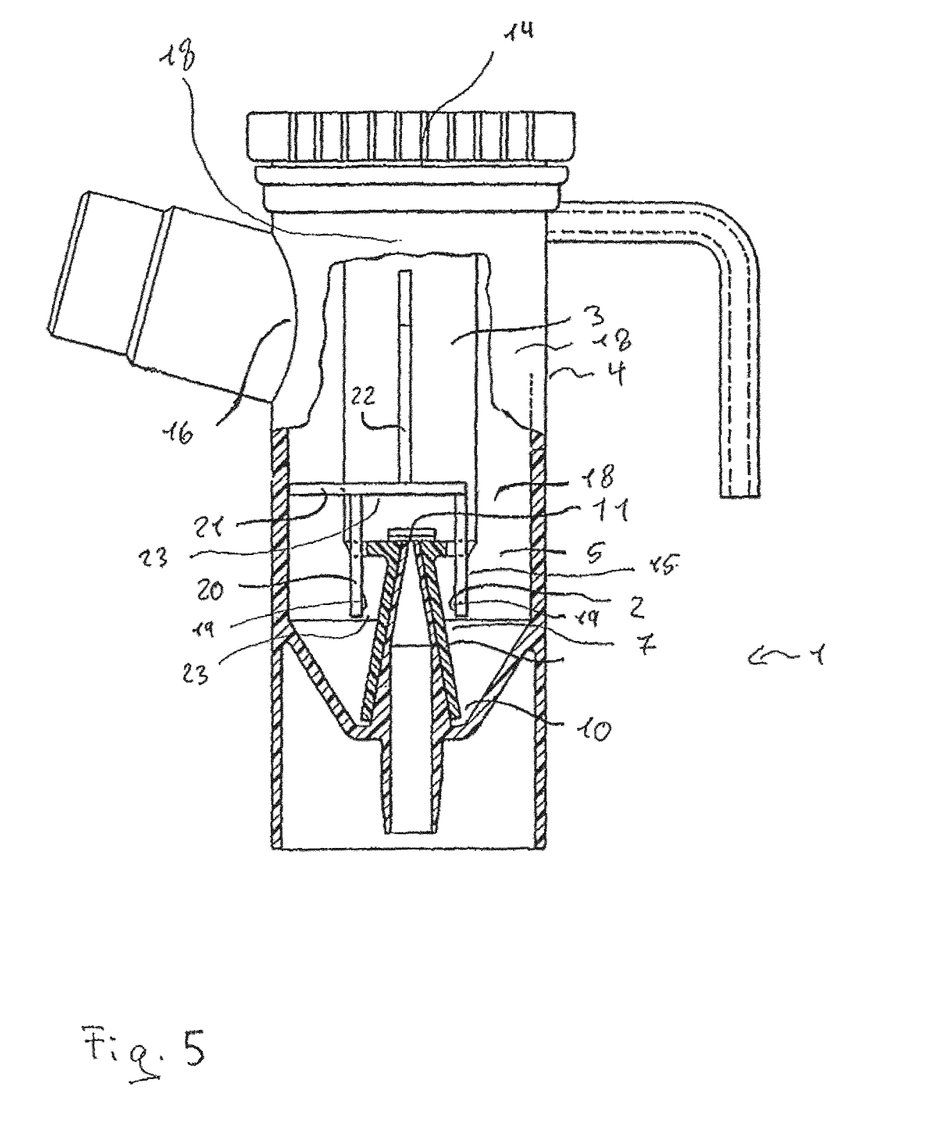
FIG. 5 shows an embodiment example of a nebulizer having a wetting surface on a baffle.

FIG. 5 shows an embodiment example of a nebulizer 1 having a wetting surface 2 on a baffle 20. The nebulizer 1 shown in FIG. 5 essentially corresponds to the nebulizer 1 shown in FIG. 1. However, it is additionally equipped with a baffle 20, a baffle section 21 and a guide section 22.

The baffle 20 is arranged in the area of the atomization region 11. It essentially has the form of a hollow cylinder and is arranged such that the atomization region 11 is disposed approximately in the middle of the longitudinal axis of the baffle 20. The baffle 20 consequently extends around the atomization region 11. The baffle 20 is open at that end face 23 which faces in the direction of the medicament reservoir 10. The end face 23 of the baffle 20 which is disposed closer to the outlet 16 is covered by the baffle section 21.

The baffle section 21 extends up to the delimiting wall 4 in a region adjacent to the outlet 16. A passage 18 is provided between the opposite region of the delimiting wall 4 and the baffle 20.

The guide section 22 extends from the baffle section 21 in the direction of the inlet opening 14. A passage 18 thereby remains between the delimiting wall 4 with the inlet opening 14 and the guide section 22. The guide section 22 extends transversely between the outlet 16 and the region of the delimiting wall 4 opposite thereto.

Upon operation of the nebulizer 1 shown in FIG. 5, an aerosol is generated according to the same principle as for the operation of the nebulizer 1 shown in FIG. 1.

Upon inhalation, the patient also sucks aerosol out of the nebulizer 1 through the outlet 16. For this to happen, the aerosol must move from the atomization region 11 to the open end face 23 of the baffle 20. The aerosol then has to change direction and pass through the passage 18 between an outer side 15 of the baffle 20 and the delimiting wall 4. From the passage 18, it must flow in the direction of the inlet opening 14 and then around the guide section 22 to the outlet 16.

This predetermined path serves to filter out undesired aerosol droplets. Aerosol droplets that are too large to follow the predetermined aerosol flow collide with the baffle 20 or the guide section 22. Only a small region for the aerosol to pass through is provided between the baffle 20 and the two-substance nozzle 7. This region is restricted even further by the medicament depending on the level of liquid in the medicament reservoir 10. The precise geometry of the baffle 20 determines the filtered-out droplet spectrum. Owing to liquid disposed on the baffle 20, both the size of the region for the aerosol to pass through is reduced and the geometry is changed. As a result hereof, more droplets are filtered out such that the output rate is low. The filtered-out droplet spectrum is also changed.

In order to minimize these effects, the entire baffle 20 is provided with a wetting surface 2. In accordance with the principle described in FIG. 3, it is achieved owing to the provision of a wetting surface 2 that flat liquid droplets 19 are formed, which cause little change to the geometry of the baffle 20 and only slightly reduce the size of the region for the aerosol to pass through.

With reference to FIGS. 1, 4 and 5, the invention has been described in connection with a two-substance nozzle. However, it is not restricted to nebulizers having this type of aerosol generator.

Figure 6:
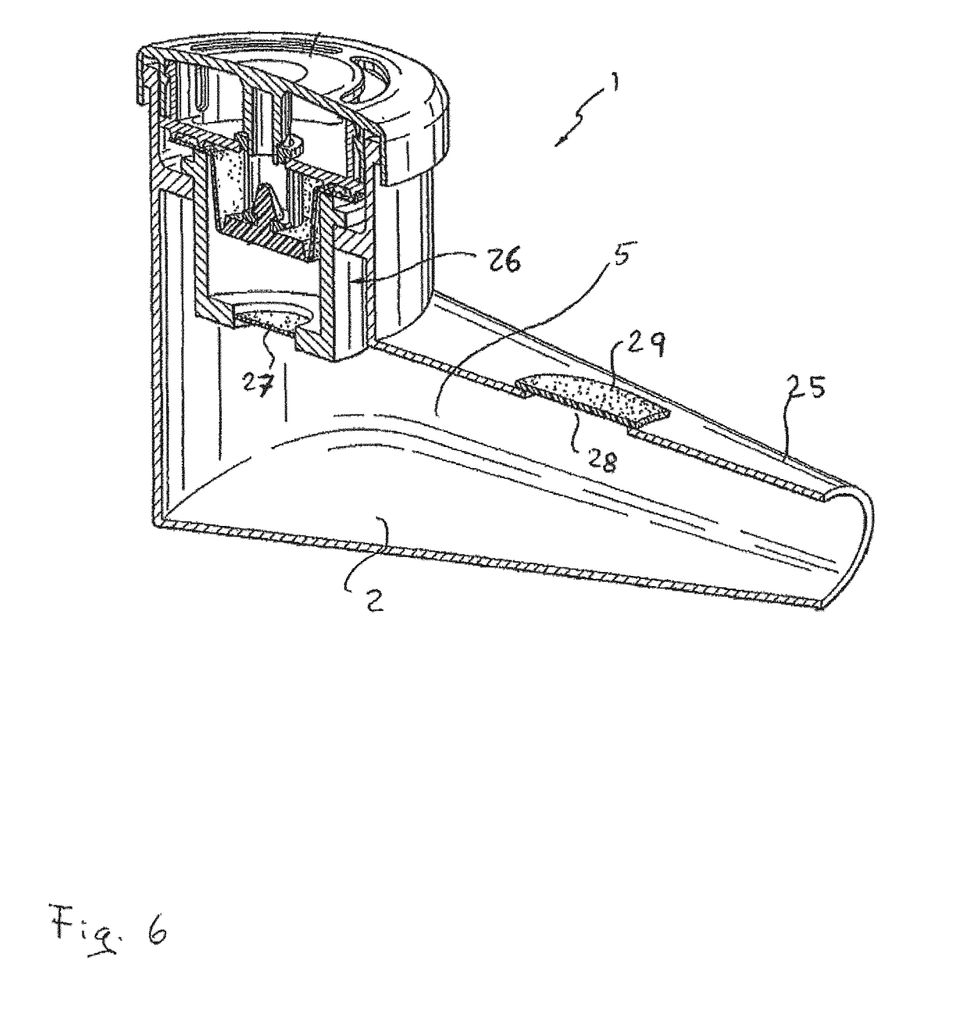
FIG. 6 shows a nebulizer comprising a nebulizing chamber, a mouthpiece and a membrane aerosol generator.

FIG. 6 shows a nebulizer 1 comprising a nebulizing chamber 5, a mouthpiece 25 and a membrane aerosol generator 26. The oscillating membrane 27 can be caused to oscillate, for example, by annular piezo elements that are not shown in the figure. During operation of the nebulizer 1, a liquid is disposed on one side of the oscillating membrane 27, at the top in FIG. 6, which is transported through openings in the oscillating membrane 27 and is released on the other side of the oscillating membrane 27, at the bottom in FIG. 6, into the nebulizing chamber 5 as an aerosol.

The nebulizing chamber 5 is provided with a wetting surface 2.

The patient can inhale the aerosol disposed in the nebulizing chamber 5 at the mouthpiece 25. So as not to cause the patient to put down the therapy device after inhaling the aerosol, the mouthpiece 25 has an exhalation opening 28 which is sealed by a flexible valve element 29. If the patient exhales into the mouthpiece 25 and thus into the nebulizing chamber 5, the flexible valve element 29 opens such that the exhaled air can exit the interior of the nebulizer 1. Upon inhalation, ambient air flows through the membrane aerosol generator 26.

LIST OF REFERENCE NUMBERS

1 Nebulizer
2 Wetting surface
3 Air inlet pipe
4 Delimiting wall
5 Nebulizing chamber
6 Aerosol generator
7 Two-substance nozzle
8 Gas channel
9 Liquid channels
10 Medicament reservoir
11 Atomization region
12 Mouth
13 Airflow control
14 Inlet opening
15 Outer side
16 Outlet
17 Fat liquid droplets
18 Passage
19 Flat liquid droplets
20 Baffle
21 Baffle section
22 Guide section
23 End face
24 Connection
25 Mouthpiece
26 Membrane aerosol generator
27 Oscillating membrane
28 Exhalation opening
29 Valve element

The invention claimed is:

1. A nebulizer comprising an aerosol generator, a nebulizing chamber, and an outlet, wherein the aerosol generator is configured to release an aerosol into the nebulizing chamber and the outlet is configured to allow removal of the aerosol from the nebulizing chamber, wherein a wetting surface is provided in the nebulizing chamber, said wetting surface being provided on a plastic component, wherein the wetting surface is configured to be wetted by the aerosol comprising a water-based liquid such that the liquid forms a contact angle of 90 degrees or less with the wetting surface, wherein the aerosol generator includes an annular aerosol guide defined by an inner wall comprising the wetting surface and an outer wall, wherein an effective cross-sectional area of the annular aerosol guide for delivery of the aerosol, when the wetting surface is wetted by the liquid, is increased in comparison with the annular aerosol guide not having the wetting surface and on which liquid is disposed, thereby increasing an output rate of the nebulizer, wherein the wetting surface comprises a fluorinated wetting surface formed directly on the plastic component and wherein hydrogen atoms of the plastic component have been replaced by fluorine atoms to form the fluorinated wetting surface.

2. The nebulizer according to claim 1, wherein the aerosol generator comprises a nozzle.

3. The nebulizer according to claim 1, wherein the nebulizing chamber comprises an aerosol guide, which connects the aerosol generator to the outlet, and the aerosol guide comprises the wetting surface.

4. The nebulizer according to claim 3, wherein a surface of the aerosol guide comprises the wetting surface.

5. The nebulizer according to claim 3, wherein an edge of the aerosol guide comprises the wetting surface.

6. The nebulizer according to claim 1, wherein the aerosol generator includes an aerosol guide and wherein the aerosol guide comprises a passage and the passage comprises the wetting surface.

7. The nebulizer according to claim 1, wherein the nebulizing chamber has a delimiting wall which comprises the wetting surface.

8. The nebulizer according to claim 1, wherein an area of the nebulizing chamber comprises a filter area, and the filter area comprises the wetting surface.

9. The nebulizer according to claim 1, wherein the nebulizing chamber comprises a baffle surface, and the baffle surface comprises the wetting surface.

10. The nebulizer according to claim 1, wherein the nebulizing chamber comprises a reservoir, the aerosol generator is configured to cooperate with the reservoir, and the reservoir comprises the wetting surface.

11. The nebulizer according to claim 1, wherein the wetting surface has a surface tension between 35 and 400 millinewtons per meter.

12. The nebulizer according to claim 1, wherein the wetting surface has a surface tension between 44 and 73 millinewtons per meter.

13. The nebulizer according to claim 1, wherein the wetting surface has a surface tension between 50 and 72 millinewtons per meter.

14. The nebulizer according to claim 1, wherein the wetting surface has an average surface roughness value between 6.3 and 0.006.

15. The nebulizer according to claim 1, wherein the wetting surface has an average surface roughness value between 1.6 and 0.01.

16. The nebulizer according to claim 1, wherein the wetting surface has an average surface roughness value between 0.5 and 0.006.

17. A method for producing a nebulizer having a wetting surface, which comprises the steps of:

producing a nebulizer comprising an aerosol generator, a nebulizing chamber and an outlet, said aerosol generator being configured to release an aerosol into the nebulizing chamber and said outlet being configured to allow removal of the aerosol from the nebulizing chamber; and providing a wetting surface on a plastic component in the nebulizing chamber, said wetting surface being provided by fluorination of the plastic component such that the aerosol comprising a water-based liquid forms a contact angle of 90 degrees or less with the wetting surface, wherein the aerosol generator includes an annular aerosol guide defined by an inner wall comprising the wetting surface and an outer wall, wherein an effective cross-sectional area of the annular aerosol guide for delivery of the aerosol, when the wetting surface is wetted by the liquid, is increased in comparison with the annular aerosol guide not having the wetting surface and on which liquid is disposed, thereby increasing an output rate of the nebulizer, and wherein hydrogen atoms of the plastic component have been replaced by fluorine atoms to form the fluorinated wetting surfacewherein providing the wetting surface comprises forming a fluorinated wetting surface directly on the plastic component.

* * * * *

UNITED STATES PATENT AND TRADEMARK OFFICE
CERTIFICATE OF CORRECTION

| | |
|---|---|
| PATENT NO. | : 11,666,712 B2 |
| APPLICATION NO. | : 15/328989 |
| DATED | : June 6, 2023 |
| INVENTOR(S) | : Uwe Schuschnig et al. |

It is certified that error appears in the above-identified patent and that said Letters Patent is hereby corrected as shown below:

In the Claims

At Column 12, Claim 17, Lines 21-26:
"thereby increasing an output rate of the nebulizer, and wherein hydrogen atoms of the plastic component have been replaced by fluorine atoms to form the fluorinated wetting surfacewherein providing the wetting surface comprises forming a fluorinated wetting surface directly on the plastic component."

Should read:
--thereby increasing an output rate of the nebulizer, wherein providing the wetting surface comprises forming a fluorinated wetting surface directly on the plastic component and wherein hydrogen atoms of the plastic component have been replaced by fluorine atoms to form the fluorinated wetting surface.--

Signed and Sealed this
Eighteenth Day of July, 2023

Katherine Kelly Vidal
*Director of the United States Patent and Trademark Office*